US008034578B2

(12) United States Patent
Nakamura et al.

(10) Patent No.: US 8,034,578 B2
(45) Date of Patent: Oct. 11, 2011

(54) PKP3 ONCOGENE AS A PROGNOSTIC INDICATOR FOR LUNG CANCER

(75) Inventors: Yusuke Nakamura, Bunkyo-ku (JP); Yataro Daigo, Bunkyo-ku (JP); Shuichi Nakatsuru, Kawasaki (JP)

(73) Assignee: Oncotherapy Science, Inc., Kawasaki-shi, Kanagawa (JP)

( * ) Notice: Subject to any disclaimer, the term of this patent is extended or adjusted under 35 U.S.C. 154(b) by 446 days.

(21) Appl. No.: 11/577,485

(22) PCT Filed: Oct. 18, 2005

(86) PCT No.: PCT/JP2005/019458
§ 371 (c)(1),
(2), (4) Date: Jan. 31, 2008

(87) PCT Pub. No.: WO2006/043692
PCT Pub. Date: Apr. 27, 2006

(65) Prior Publication Data
US 2008/0254452 A1 Oct. 16, 2008

Related U.S. Application Data

(60) Provisional application No. 60/620,405, filed on Oct. 19, 2004.

(51) Int. Cl.
*G01N 33/574* (2006.01)
*G01N 33/566* (2006.01)
*G01N 33/567* (2006.01)
*G01N 33/53* (2006.01)
*C12Q 1/68* (2006.01)

(52) U.S. Cl. ............. 435/7.23; 435/6; 435/7.1; 435/7.2; 435/7.21; 436/501; 436/503; 436/63; 436/64

(58) Field of Classification Search ............... 435/6, 7.1, 435/7.2, 7.21, 7.23; 436/501, 503, 63, 64
See application file for complete search history.

(56) References Cited

U.S. PATENT DOCUMENTS
2006/0024692 A1  2/2006 Nakamura et al.

FOREIGN PATENT DOCUMENTS
WO   WO 00/66619 A2     11/2000
WO   WO02/086443    *  10/2002
WO   WO 2004/031413 A2   4/2004
WO   WO 2005/089735 A2   9/2005

OTHER PUBLICATIONS

Aigner, K., et al. FEBS Letters, 851: 1617-1624, 2007.*
Kundu, S. T., et al. Int. J. Cancer, 123: 2303-2314, 2008.*
Heighway J, Betticher DC. Lung: Non-small cell carcinoma. Atlas Genet and Cytogenet Oncology Haematol, Feb. 2004.*
Bonné, S., et al., "Plakophilin-3, a novel Armadillo-like protein present in nuclei and desmosomes of epithelial cells," Jul. 1999, *J. Cell Sci.*, vol. 112, pp. 2265-2276.
Bonné, S., et al., "Defining desmosomal plakophilin-3 interactions," Apr. 2003, *J. Cell Biol.*, vol. 161, pp. 403-416.
Callagy, G., et al., "Molecular classification of breast carcinomas using tissue microarrays," Mar. 2003, *Diagn. Mol. Pathol.*, vol. 12, pp. 27-34.
Chin, S.F., et al., "A simple and reliable pretreatment protocol facilitates fluorescent in situ hybridisation on tissue microarrays of paraffin wax embedded tumour samples," Oct. 2003, *Mol. Pathol.*, vol. 56, pp. 275-279.
Cojocaru, G., et al., "Transcriptional profiling of non-small cell lung cancer using oligonucleotide microarrays," Mar. 2002, *Chest*, vol. 121, 44S.
Fujii, T., et al., "A preliminary transcriptome map of non-small cell lung cancer,"Jun. 2002, *Cancer Res.*, vol. 62, pp. 3340-3346.
Furukawa, C., et al., "Plakophilin 3 oncogene as prognostic marker and therapeutic target for lung cancer," Aug. 2005, *Cancer Res.*, vol. 65, pp. 7102-7110.
Heighway, J., et al., "Expression profiling of primary non-small cell lung cancer for target identification," Oct. 2002, *Oncogene*, vol. 21, pp. 7749-7763.
Kikuchi, T., et al., "Expression profiles of non-small cell lung cancers on cDNA microarrays: Identification of genes for prediction of lymph-node metastasis and sensitivity to anti-cancer drugs," Apr. 2003, *Oncogene*, vol. 22, pp. 2192-2205.
Kononen, J., et al., "Tissue microarrays for high-throughput molecular profiling of tumor specimens," Jul. 1998, *Nat. Med.*, vol. 4, 844-847.
Papagerakis, S., et al., "Immunohistochemical localization of plakophilins (PKP1, PKP2, PKP3, and p0071) in primary oropharyngeal tumors: correlation with clinical parameters," Jun. 2003, *Human Pathol.*, vol. 34, pp. 565-572.
Sauter, G., et al., "Tissue microarrays in drug discovery," Dec. 2003, *Nat. Rev. Drug Discov.*, vol. 2, pp. 962-972.
Schmidt, A., et al., "Plakophilin-3—a novel cell-type-specific desmosomal plaque protein," Jun. 1999, *Differentiation*, vol. 64, pp. 292-306.
Wang, T., et al., "Identification of genes differentially over-expressed in lung squamous cell carcinoma using combination of cDNA subtraction and microarray analysis," Mar. 2000, *Oncogene*, vol. 19, pp. 1519-1528.
Wigle, D., et al., "Molecular profiling of non-small cell lung cancer and correlation with disease-free survival," Jun. 2002, *Cancer Res.*, vol. 62, pp. 3005-3008. Cheng, G., et al., "Protein profiles associated with survival in lung adenocarcinoma," *Proc Natl Acad Sci USA*, vol. 100(23), pp. 13537-13542 (Nov. 11, 2003, Epub Oct. 22, 2003).
Sasaki, H., et al., "The investigation of gene analysis for development and metastasis in lung adenocarcinoma—using LightCycler," *The Journal of the Japanese Association for Chest Surgery*, vol. 18(3), p. 200, Abstract P-135 (2004).

* cited by examiner

*Primary Examiner* — Alana M Harris
*Assistant Examiner* — Anne Holleran
(74) *Attorney, Agent, or Firm* — Kilpatrick Townsend & Stockton LLP

(57) ABSTRACT

The present invention provides the method of predicting an non-small cell lung cancer (NSCLC) prognosis.

2 Claims, 1 Drawing Sheet

SEQUENCE LISTING

```
<160> NUMBER OF SEQ ID NOS: 2

<210> SEQ ID NO 1
<211> LENGTH: 2831
<212> TYPE: DNA
<213> ORGANISM: Homo sapiens

<400> SEQUENCE: 1
gaattccgga caggacgtga agatagttgg gtttggaggc ggccgccagg cccaggcccg      60
gtggacctgc cgccatgcag gacggtaact tcctgctgtc ggccctgcag cctgaggccg     120
```

-continued

```
gcgtgtgctc cctggcgctg ccctctgacc tgcagctgga ccgccggggc gccgaggggc    180
cggaggccga gcggctgcgg gcagcccgcg tccaggagca ggtccgcgcc cgcctcttgc    240
agctgggaca gcagccgcgg cacaacgggg ccgctgagcc cgagcctgag gccgagactg    300
ccagaggcac atccaggggg cagtaccaca ccctgcaggc tggcttcagc tctcgctctc    360
agggcctgag tggggacaag acctcggggct tccggcccat cgccaagccg gcctacagcc    420
cagcctcctg gtcctcccgc tccgccgtgg atctgagctg cagtcggagg ctgagttcag    480
cccacaatgg gggcagcgcc tttggggccg ctgggtacgg gggtgcccag cccacccctc    540
ccatgcccac caggcccgtg tccttccatg agcgcggtgg ggttgggagc cgggccgact    600
atgacacact ctccctgcgc tcgctgcggc tggggcccgg gggcctggac gaccgctaca    660
gcctggtgtc tgagcagctg gagcccgcgg ccacctccac ctacagggcc tttgcgtacg    720
agcgccaggc cagctccagc tccagccggg caggggggct ggactggccc gaggccactg    780
aggtttcccc gagccggacc atccgtgccc ctgccgtgcg gaccctgcag cgattccaga    840
gcagccaccg gagccgcggg gtaggcgggg cagtgccggg ggccgtcctg gagccagtgg    900
ctcgagcgcc atctgtgcgc agcctcagcc tcagcctggc tgactcgggc cacctgccgg    960
acgtgcatgg gttcaacagc tacggtagcc accgaaccct gcagagactc agcagcggtt   1020
ttgatgacat tgacctgccc tcagcagtca agtacctcat ggcttcagac cccaacctgc   1080
aggtgctggg agcggcctac atccagcaca gtgctacag cgatgcagcc gccaagaagc    1140
aggcccgcag ccttcaggcc gtgcctaggc tggtgaagct cttcaaccac gccaaccagg   1200
aagtgcagcg ccatgccaca ggtgccatgc gcaacctcat ctacgacaac gctgacaaca   1260
agctggccct ggtggaggag aacgggatct tcgagctgct gcggacactg cgggagcagg   1320
atgatgagct tcgcaaaaat gtcacaggga tcctgtggaa ccttcatcc agcgaccacc    1380 tgaaggaccg cctggccaga gacacgctgg agcagctcac ggacctggtg ttgagccccc   1440
tgtcgggggc tggggtccc cccctcatcc agcagaacgc ctcggaggcg agatcttct     1500 acaacgccac cggcttcctc aggaacctca gctcagcctc tcaggccact cgccagaaga   1560
tgcgggagtg ccacgggctg gtggacgccc tggtcacctc tatcaaccac gccctggacg   1620
cgggcaaatg cgaggacaag agcgtggaga acgcggtgtg cgtcctgcgg aacctgtcct   1680
accgcctcta cgacgagatg ccgccgtccg cgctgcagcg gctggagggt cgcggccgca   1740
gggacctggc gggggcgccg ccgggagagg tcgtgggctg cttcacgccg cagagccggc   1800
ggctgcgcga gctgcccctc gccgccgatg cgctcacctt cgcggaggtg tccaaggacc   1860
ccaagggcct cgagtggctg tggagccccc agatcgtggg gctgtacaac cggctgctgc   1920
agcgctgcga gctcaaccgg cacacgacgg aggcggccgc cggggcgctg cagaacatca   1980
cggcaggcga ccgcaggtgg gcggggggtgc tgagccgcct ggccctggag caggagcgta   2040
ttctgaaccc cctgctagac cgtgtcagga ccgccgacca ccaccagctg cgctcactga   2100
ctggcctcat ccgaaacctg tctcggaacg ctaggaacaa ggacgagatg tccacgaagg   2160
tggtgagcca cctgatcgag aagctgccag gcagcgtggg tgagaagtcg cccccagccg   2220
aggtgctggt caacatcata gctgtgctca acaacctggt ggtggccagc ccatcgctg    2280 cccgagacct gctgtatttt gacggactcc gaaagctcat cttcatcaag aagaagcggg   2340
acagccccga cagtgagaag tcctccccggg cagcatccag cctcctggcc aacctgtggc   2400
agtacaacaa gctccaccgt gactttcggg cgaagggcta tcggaaggag gacttcctgg   2460
gcccataggt gaagccttct ggaggagaag gtgacgtggc ccagcgtcca agggacagac   2520
```

```
tcagctccag gctgcttggc agcccagcct ggaggagaag gctaatgacg gaggggcccc    2580
tcgctggggc ccctgtgtgc atctttgagg gtcctgggcc accaggaggg gcagggtctt    2640
atagctgggg acttggcttc cgcagggcag ggggtggggc agggctcaag gctgctctgg    2700
tgtatggggt ggtgacccag tcacattggc agaggtgggg gttggctgtg gcctggcagt    2760
atcttgggat agccagcact gggaataaag atggccatga acagtcacaa aaaaaaaaa    2820 aaaaggaatt c                                                        2831

<210> SEQ ID NO 2
<211> LENGTH: 797
<212> TYPE: PRT
<213> ORGANISM: Homo sapiens

<400> SEQUENCE: 2

Met Gln Asp Gly Asn Phe Leu Leu Ser Ala Leu Gln Pro Glu Ala Gly
1               5                   10                  15

Val Cys Ser Leu Ala Leu Pro Ser Asp Leu Gln Leu Asp Arg Arg Gly
                20                  25                  30

Ala Glu Gly Pro Glu Ala Glu Arg Leu Arg Ala Arg Val Gln Glu
            35                  40                  45

Gln Val Arg Ala Arg Leu Leu Gln Leu Gly Gln Gln Pro Arg His Asn
    50                  55                  60

Gly Ala Ala Glu Pro Glu Pro Glu Ala Glu Thr Ala Arg Gly Thr Ser
65                  70                  75                  80

Arg Gly Gln Tyr His Thr Leu Gln Ala Gly Phe Ser Arg Ser Gln
                85                  90                  95

Gly Leu Ser Gly Asp Lys Thr Ser Gly Phe Arg Pro Ile Ala Lys Pro
            100                 105                 110

Ala Tyr Ser Pro Ala Ser Trp Ser Ser Arg Ser Ala Val Asp Leu Ser
        115                 120                 125

Cys Ser Arg Arg Leu Ser Ser Ala His Asn Gly Gly Ser Ala Phe Gly
    130                 135                 140

Ala Ala Gly Tyr Gly Gly Ala Gln Pro Thr Pro Pro Met Pro Thr Arg
145                 150                 155                 160

Pro Val Ser Phe His Glu Arg Gly Gly Val Gly Ser Arg Ala Asp Tyr
                165                 170                 175

Asp Thr Leu Ser Leu Arg Ser Leu Arg Leu Gly Pro Gly Gly Leu Asp
            180                 185                 190

Asp Arg Tyr Ser Leu Val Ser Glu Gln Leu Glu Pro Ala Ala Thr Ser
        195                 200                 205

Thr Tyr Arg Ala Phe Ala Tyr Glu Arg Gln Ala Ser Ser Ser Ser
    210                 215                 220

Arg Ala Gly Gly Leu Asp Trp Pro Glu Ala Thr Glu Val Ser Pro Ser
225                 230                 235                 240

Arg Thr Ile Arg Ala Pro Ala Val Arg Thr Leu Gln Arg Phe Gln Ser
                245                 250                 255

Ser His Arg Ser Arg Gly Val Gly Gly Ala Val Pro Gly Ala Val Leu
            260                 265                 270

Glu Pro Val Ala Arg Ala Pro Ser Val Arg Ser Leu Ser Leu Ser Leu
        275                 280                 285

Ala Asp Ser Gly His Leu Pro Asp Val His Gly Phe Asn Ser Tyr Gly
    290                 295                 300

Ser His Arg Thr Leu Gln Arg Leu Ser Ser Gly Phe Asp Ile Asp
305                 310                 315                 320
```

-continued

```
Leu Pro Ser Ala Val Lys Tyr Leu Met Ala Ser Asp Pro Asn Leu Gln
            325                 330                 335
Val Leu Gly Ala Ala Tyr Ile Gln His Lys Cys Tyr Ser Asp Ala Ala
            340                 345                 350
Ala Lys Lys Gln Ala Arg Ser Leu Gln Ala Val Pro Arg Leu Val Lys
            355                 360                 365
Leu Phe Asn His Ala Asn Gln Glu Val Gln Arg His Ala Thr Gly Ala
            370                 375                 380
Met Arg Asn Leu Ile Tyr Asp Asn Ala Asp Asn Lys Leu Ala Leu Val
385                 390                 395                 400
Glu Glu Asn Gly Ile Phe Glu Leu Leu Arg Thr Leu Arg Glu Gln Asp
                405                 410                 415
Asp Glu Leu Arg Lys Asn Val Thr Gly Ile Leu Trp Asn Leu Ser Ser
            420                 425                 430
Ser Asp His Leu Lys Asp Arg Leu Ala Arg Asp Thr Leu Glu Gln Leu
            435                 440                 445
Thr Asp Leu Val Leu Ser Pro Leu Ser Gly Ala Gly Gly Pro Pro Leu
            450                 455                 460
Ile Gln Gln Asn Ala Ser Glu Ala Glu Ile Phe Tyr Asn Ala Thr Gly
465                 470                 475                 480
Phe Leu Arg Asn Leu Ser Ser Ala Ser Gln Ala Thr Arg Gln Lys Met
                485                 490                 495
Arg Glu Cys His Gly Leu Val Asp Ala Leu Val Thr Ser Ile Asn His
            500                 505                 510
Ala Leu Asp Ala Gly Lys Cys Glu Asp Lys Ser Val Glu Asn Ala Val
            515                 520                 525
Cys Val Leu Arg Asn Leu Ser Tyr Arg Leu Tyr Asp Glu Met Pro Pro
            530                 535                 540
Ser Ala Leu Gln Arg Leu Glu Gly Arg Gly Arg Arg Asp Leu Ala Gly
545                 550                 555                 560
Ala Pro Pro Gly Glu Val Val Gly Cys Phe Thr Pro Gln Ser Arg Arg
                565                 570                 575
Leu Arg Glu Leu Pro Leu Ala Ala Asp Ala Leu Thr Phe Ala Glu Val
            580                 585                 590
Ser Lys Asp Pro Lys Gly Leu Glu Trp Leu Trp Ser Pro Gln Ile Val
            595                 600                 605
Gly Leu Tyr Asn Arg Leu Leu Gln Arg Cys Glu Leu Asn Arg His Thr
            610                 615                 620
Thr Glu Ala Ala Ala Gly Ala Leu Gln Asn Ile Thr Ala Gly Asp Arg
625                 630                 635                 640
Arg Trp Ala Gly Val Leu Ser Arg Leu Ala Leu Glu Gln Glu Arg Ile
                645                 650                 655
Leu Asn Pro Leu Leu Asp Arg Val Arg Thr Ala Asp His His Gln Leu
            660                 665                 670
Arg Ser Leu Thr Gly Leu Ile Arg Asn Leu Ser Arg Asn Ala Arg Asn
            675                 680                 685
Lys Asp Glu Met Ser Thr Lys Val Val Ser His Leu Ile Glu Lys Leu
            690                 695                 700
Pro Gly Ser Val Gly Glu Lys Ser Pro Ala Glu Val Leu Val Asn
705                 710                 715                 720
Ile Ile Ala Val Leu Asn Asn Leu Val Val Ala Ser Pro Ile Ala Ala
                725                 730                 735
Arg Asp Leu Leu Tyr Phe Asp Gly Leu Arg Lys Leu Ile Phe Ile Lys
```

-continued

```
                            740                     745                     750
Lys Lys Arg Asp Ser Pro Asp Ser Glu Lys Ser Ser Arg Ala Ala Ser
        755                     760                 765

Ser Leu Leu Ala Asn Leu Trp Gln Tyr Asn Lys Leu His Arg Asp Phe
    770                 775                 780

Arg Ala Lys Gly Tyr Arg Lys Glu Asp Phe Leu Gly Pro
785                 790                 795
```

PKP3 ONCOGENE AS A PROGNOSTIC INDICATOR FOR LUNG CANCER

PRIORITY

This application is a U.S. National Phase of PCT/JP2005/019458, filed Oct. 18, 2005, which claims the benefit of U.S. provisional application Ser. No. 60/620,405 filed Oct. 19, 2004. The contents of all of the aforementioned applications are herein incorporated by reference in their entirety.

TECHNICAL FIELD

The present invention relates to the field of biological science, more specifically to the field of cancer research. In particular, the invention relates to the use of the expression level of lung cancer associated gene PKP3 as a prognostic indicator for lung cancer.

BACKGROUND OF THE INVENTION

Lung cancer is the leading cause of cancer deaths worldwide, and non-small cell lung cancer (NSCLC) accounts for nearly 80% of those cases (Greenlee R T, et al. (2001) CA Cancer J Clin 51(1):15-36.). Many genetic alterations associated with the development and progression of lung cancer have been reported. Nevertheless, the precise molecular mechanisms remain unclear (Sozzi G. (2001) Eur J Cancer 37 Suppl 7:S63-73.). Within the last decade, several newly-developed cytotoxic agents, such as paclitaxel, docetaxel, gemcitabine, and vinorelbine, have begun to offer multiple choices for treatment of patients with advanced lung cancer; however, each of these regimens confers only a modest survival benefit as compared with cisplatin-based therapies (Schiller J H, et al. (2002) N Engl J Med 346(2):92-8.; Kelly K, et al (2001) J Clin Oncol 19(13):3210-8.). Alternatively, by the genome wide cDNA microarray analysis, 642 up-regulated genes and 806 down-regulated genes have been identified as potential diagnostic markers and/or therapeutic targets for NSCLC (WO 2004/31413).

BRIEF SUMMARY OF THE INVENTION

Systematic analysis of the expression levels of thousands of genes in tumors is an effective approach for selecting candidates for use in the development of novel tumor markers (Kikuchi T, et al. (2003) Oncogene 22(14):2192-205.; Kakiuchi S, et al. (2003) Mol Cancer Res 1(7):485-99.; Zembutsu H, et al. (2003) Int J Oncol 23(1):29-39.; Suzuki C, et al. (2003) Cancer Res 63(21):7038-41.; Ochi K, et al. (2004) Int J Oncol 24(3):647-55.). The present inventors have been attempting to isolate potential molecular targets for diagnosis of lung cancer by analyzing genome-wide expression profiles of NSCLC cells on a cDNA microarray containing 23,040 genes, using pure populations of tumor cells prepared from 37 cancer tissues by laser-capture microdissection (Kikuchi T, et al. (2003) Oncogene 22(14):2192-205.). In the course of those studies, 642 up-regulated genes and 806 down-regulated genes have been identified as potential diagnostic markers and/or therapeutic targets for NSCLC (WO 2004/31413). Among them, frequent transactivation of the gene encoding plakophilin 3 (PKP3; GenBank Accession No. NM_007183, SEQ ID No. 1, 2) was observed in primary NSCLC.

PKP3 is a member of the p120$^{ctn}$/plakophilin subfamily of armadillo (ARM) proteins that are synthesized in cells of stratified and single-layered epithelia; armadillo molecules provide physical links between selectively synthesized desmosomal proteins (Schmidt A, et al. (1999) Differentiation 64(5):291-306.; Bonne S, et al. (2003) J Cell Biol 161(2):403-16.; Bonne S, et al. (1999) J Cell Sci 112(Pt 14):2265-76.). While ARM-related proteins in general have structural roles in cell-contact and cytoskeleton-associated activities, they can also exert signaling functions by generating and transducing signals that affect gene expression. Multiple studies have implied that genetic aberrations in members of the ARM-protein family, including plakoglobin (PKGB), β-catenin (CTNNB1), and adenomatous polyposis coli (APC), contribute to tumor development and/or progression (Papagerakis S, et al. (2003) Hum Pathol 34(6):565-72.; Satoh S, et al. (2000) Nat Genet 24(3):245-50.). The lower expression of PKP3 in normal tissues, elevated expression in NSCLCs, and reduced growth, proliferation and/or survival of the transfected cells by the suppression of this gene suggest that it might be useful as a novel diagnostic marker and/or target for new drugs and immunotherapy (WO2004/31413). However, the role of the PKP3 during carcinogenesis, or even its function in normal epithelial cells, has not been fully clarified.

Herein, evidence is presented that plakophilin 3 (PKP3) functions a prognostic indicator of lung cancer. Specifically, a high level of PKP3 expression was associated with poor survival as well as disease stage and node status for patients with lung adenocarcinoma (ADC), suggesting an important role for the PKP3 protein in the development and progression of this disease. As the data herein suggest that up-regulation of PKP3 is a frequent and important feature of lung carcinogenesis, the present inventors accordingly propose that targeting the PKP3 molecule holds promise for development of new diagnostic strategies for clinical management of lung cancers.

Accordingly, it is an object of the present invention to provide a method for assessing or determining the prognosis of a patient with non-small cell lung cancer by comparing a PKP3 level in a patient-derived biological sample with that of a control sample. An elevated expression level is indicative of poor survival. In particular, the higher the expression level of PKP3 measured in the patient derived sample, the poorer the prognosis for post-treatment remission, recovery and/or survival and the higher the likelihood of poor clinical outcome.

It is a further object of the present invention to provide kits for assessing an NSCLC prognosis, such kits including PKP3-detection reagents. The expression level of PKP3 may be determined by (a) detecting transcription products of the PKP3 gene, such as mRNA; (b) detecting the PKP3 protein, or (c) detecting the biological activity of the PKP3 protein. The subject-derived biological sample may be any sample derived from a subject, e.g., a patient known to have or suspected of having non-small cell lung cancer. Examples of suitable biological samples include, but are not limited to, sputum, blood, serum, plasma or cancer tissue. In a preferred embodiment, the biological sample is a body fluid, more preferably blood or a blood derived sample.

These and other objects of the invention will be evident from the following description, taken together with the attached drawings and appended claims. It is to be understood that both the foregoing summary of the invention and the following detailed description are of a preferred embodiment, and not restrictive of the invention or other alternate embodiments of the invention.

BRIEF DESCRIPTION OF THE DRAWINGS

FIGS. 1A-1D depict the immunohistochemical evaluation of PKP3 expression on tissue microarrays (X100).

Figure 1:
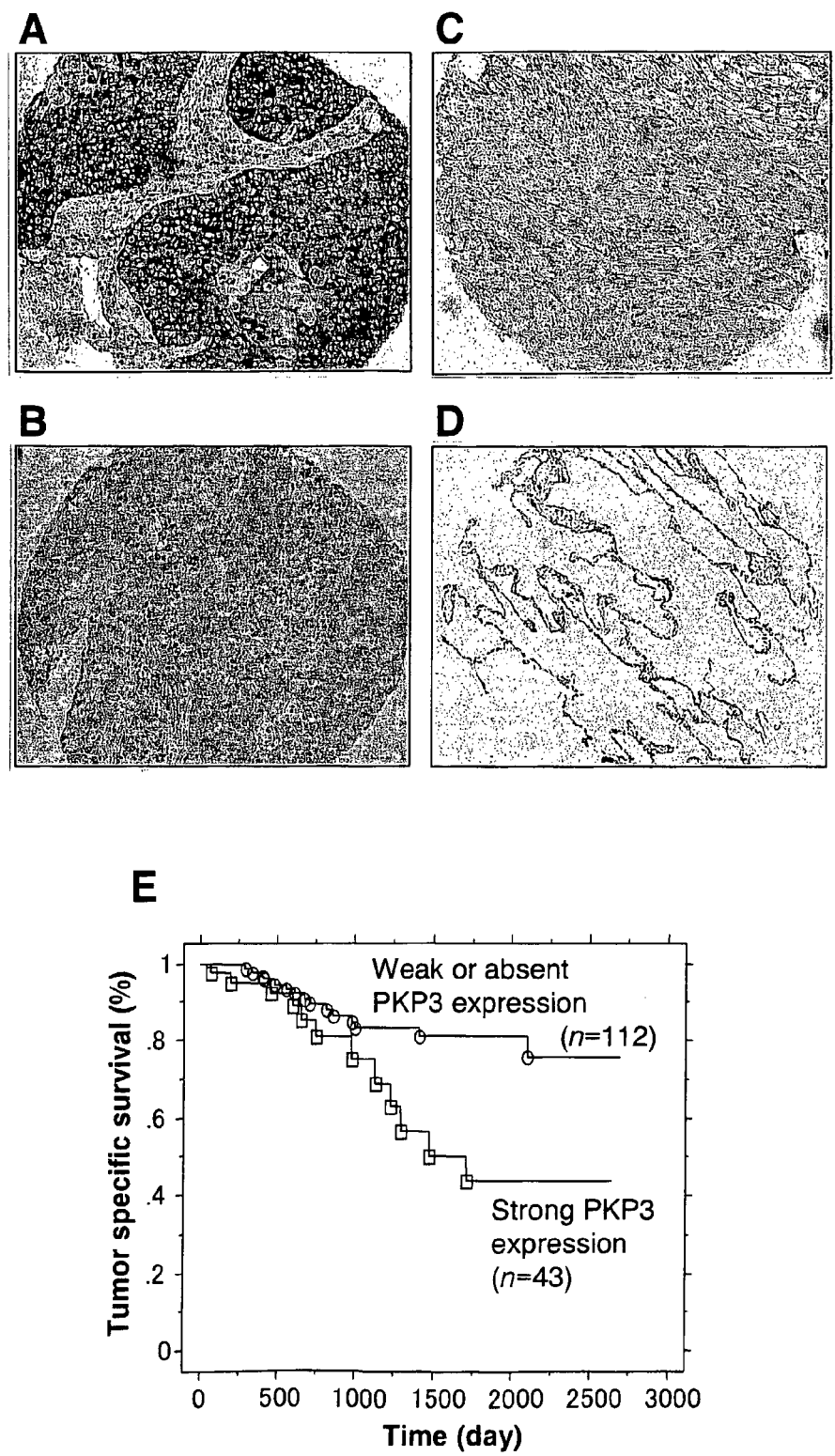
FIG. 1 depicts the association of PKP3 over-expression with poor clinical outcomes among NSCLC patients. In particular.

Examples are shown of strong (A), weak (B), and absent (C) PKP3 expression in lung SCCs, and of no expression in normal lung (D). E, Kaplan-Meier analysis of tumor-specific survival in patients with ADC according to PKP3 expression (P=0.009; Log-rank test).

DETAILED DESCRIPTION OF THE INVENTION

The words "a", "an", and "the" as used herein mean "at least one" unless otherwise specifically indicated.

The PKP3 cDNA consists of 2831 nucleotides that contain an open reading frame of 2394 nucleotides as set forth in SEQ. ID. NO.: 1. The open reading frame encodes a 797-amino acid protein having amino acid sequence as set forth in SEQ. ID. NO.: 2.

PKP3 is a member of the p120$^{ctn}$/plakophilin subfamily of armadillo (ARM) proteins that are synthesized in cells of stratified and single-layered epithelia; armadillo molecules provide physical links between selectively synthesized desmosomal proteins (Schmidt A, et al. (1999) Differentiation 64(5):291-306.; Bonne S, et al. (2003) J Cell Biol 161(2):403-16.; Bonne S, et al. (1999) J Cell Sci 112(Pt 14):2265-76.). While ARM-related proteins in general have structural roles in cell-contact and cytoskeleton-associated activities, they can also exert signaling functions by generating and transducing signals that affect gene expression. Multiple studies have implied that genetic aberrations in members of the ARM-protein family, including plakoglobin (PKGB), β-catenin (CTNNB1), and adenomatous polyposis coli (APC), contribute to tumor development and/or progression (Papagerakis S, et al. (2003) Hum Pathol 34(6):565-72.; Satoh S, et al. (2000) Nat Genet 24(3):245-50.).

As used herein, the phrase "control level" refers to a PKP3 expression level associated with a known disease state (e.g., disease-free, positive prognosis group, early stage, etc.). The control level may correspond to a single measurement associated with a single known sample or to a database of expression patterns from previously tested cells.

Herein, in the context of cancer treatment, the term "efficacious" refers to a treatment that leads to a reduction in the expression of PKP3 or a decrease in size, prevalence or metastatic potential of non-small cell lung cancer in a subject. When a treatment is applied prophylactically, "efficacious" means that the treatment retards or prevents occurrence of non-small cell lung cancer or alleviates a clinical symptom of non-small cell lung cancer. The assessment of non-small cell lung cancer can be made using standard clinical protocols. Furthermore, the efficaciousness of a treatment may be determined in association with any known method for diagnosing or treating non-small cell lung cancer. For example, non-small cell lung cancer is diagnosed histopathologically or by identifying symptomatic anomalies such as chronic cough, hoarseness, coughing up blood, weight loss, loss of appetite, shortness of breath, wheezing, repeated bouts of bronchitis or pneumonia and chest pain.

In the context of assessing the prognosis of a patient with the non-small cell lung cancer, involving the step of comparing the expression level of PKP3 in the patient-derived biological sample with a control level, an increase in the expression level of PKP3 expression indicates a less favorable prognosis. The term "prognosis" refers to a forecast as to the probable outcome of the disease as well as the prospect of recovery from the disease as indicated by the nature and symptoms of the case. Accordingly, a negative or poor prognosis is defined by a lower post-treatment survival term or survival rate. Conversely, a positive or good prognosis is defined by an elevated post-treatment survival term or survival rate.

Unless otherwise defined, all technical and scientific terms used herein have the same meaning as commonly understood by one of ordinary skill in the art to which this invention belongs. In case of conflict, the present specification, including definitions, will control.

The present invention is based on the finding that a relatively high expression level of PKP3 (as compared to a control level) is associated with poor prognosis in non-small cell lung cancer (NSCLC) patients. In view of the evidence provided herein, that PKP3 expression is associated with poor prognosis of cancer patients such as lung adenocarcinoma, the present invention provides methods for determining a prognosis for cancer patients. In one embodiment, the method of the present invention comprises the steps of:
  a. detecting a PKP3 expression level in a specimen collected from a subject whose NSCLC prognosis is to be predicted, and
  b. indicating a poor prognosis when the PKP3 expression detected is elevated as compared to a control level associated with a positive prognosis.

The present invention provides a method for assessing or determining a prognosis of a lung cancer patient. For the purposes of this invention, the term "prognosis" is intended to encompass predictions and likelihood analysis of lung cancer progression, particularly NSCLC recurrence, metastatic spread and disease relapse. The prognostic methods of the present invention are intended to be used clinically in making decisions concerning treatment modalities, including therapeutic intervention, diagnostic criteria such as disease staging, and disease monitoring and surveillance for metastasis or recurrence of neoplastic disease.

NSCLC prognosis and progression of the disease can be predicted by the present invention. In particular, the present invention is useful for prediction of prognosis of lung adenocarcinoma (ADC). In the context of the present invention, NSCLC prognosis is predicted by measuring the expression level of PKP3 in a test population of cells, (i.e., a patient-derived biological sample). Preferably, the test cell population contains an epithelial cell, e.g., a cell obtained from lung tissue. Gene expression can also be measured from blood or other bodily fluids, such as sputum. Other biological samples can be used to determine protein level. For example, the level of protein in blood or serum derived from a subject to be assessed can be measured by immunoassay or other conventional biological assays. These test samples may be obtained from the subject at various points in time, including before, during and/or after the treatment.

In the context of the present invention, expression of PKP3 is determined in the test cell or biological sample and compared to expression level associated with a control sample. In this context, a standard value of PKP3 expression level associated with a good prognosis group may be useful as a control level of the present method. In the present method, when the PKP3 expression level in a sample specimen is high as compared with that of control level, then the sample is deemed to have an elevated level of PKP3 expression. The standard value may be obtained by any method known in the art. For example, a range of mean±2 S.D. or mean±3 S.D. may be used as standard value. The expression levels of PKP3 in the control samples and the specimen from the subject may be determined at the same time.

Alternatively, a determination of poor prognosis can result when strong staining is observed by immunohistochemical analysis of sample tissue. In order to predict poor prognosis, the strength of staining of the specimen can be assessed by comparing it with a control reagent providing strong staining result. The control reagent may be prepared from PKP3 expressing cells or from tissue whose expression level is controlled to adjust to that of strong staining sample. PKP3 expressing cells may comprise cells or cell lines derived from tumor. Furthermore, PKP3 expressing cells also may be prepared by transfection of suitable host cell with PKP3 expressing vector.

In the present invention, "assessment of prognosis" means that a prognosis of a NSCLC patient is determined. When the PKP3 expression level in a subject sample falls within the range associated with a control sample, the subject is predicted to have good prognosis. On the contrary, when the PKP3 expression level in a subject sample exceeds the range associated with a control sample, the subject is predicted to have poor prognosis. For example, an increase in the level of expression of PKP3 in a patient-derived tissue sample as compared to a control sample indicates that the subject has poor prognosis. In other words, when the expression level of PKP3 is closer to the expression level in the good prognosis group, the subject is predicted to have good prognosis.

In the present method, the expression level of PKP3 may be detected by any one of the method selected from the group consisting of:
(a) detecting the mRNA encoding the amino acid sequence of SEQ ID NO: 2,
(b) detecting the protein comprising the amino acid sequence of SEQ ID NO: 2, and
(c) detecting the biological activity of the protein comprising the amino acid sequence of SEQ ID NO: 2.

In the present invention, the mRNA, the protein, or the biological activity of the protein may be detected by any methods. Methods for detecting a given protein, mRNA or biological activity thereof are well known to those skilled in the art. For example, the mRNA may be detected using known PCR or hybridization based technologies. Alternatively, any immunoassay format may be applied to detect the protein. The biological activity of PKP3 can be also determined using any suitable method.

In the present invention, assessment of a poor prognosis may be used to determine further treatment, e.g., to stop further treatments that reduce quality of life, to treat the cancer in a different manner than previously used or to treat the cancer more aggressively. Accordingly, the assessment of prognosis using PKP3 expression levels as a indicator should eventually enable clinicians to choose, in advance, the most appropriate treatment for each individual NSCLC patient, without requiring the information of conventional clinical staging of the disease and using only routine procedures for tissue-sampling.

The present invention also provides kits for assessing an NSCLC prognosis, such kits including PKP3-detection reagents. For example, in the context of the present invention, the PKP3 detecting reagent may comprise any one or more component selected from the group consisting of:
(a) a reagent for detecting the mRNA encoding the amino acid sequence of SEQ ID NO: 2,
(b) a reagent for detecting the protein comprising the amino acid sequence of SEQ ID NO: 2, and
(c) a reagent for detecting the biological activity of the protein comprising the amino acid sequence of SEQ ID NO: 2.

Suitable PKP3-detection reagents include nucleic acids that specifically bind to or identify a PKP3 nucleic acid, such as oligonucleotide sequences which are complementary to a portion of the PKP3 nucleic acid sequence or antibodies that bind to proteins encoded by a PKP3 nucleic acid.

The PKP3-detection reagents may be packaged together in the form of a kit. For example, the reagents may be packaged in separate containers, e.g., a nucleic acid or antibody (either bound to a solid matrix or packaged separately with reagents for binding it to the matrix) in one container, a control reagent (positive and/or negative) in a second container, and/or a detectable label in a third container. Tissue samples obtained from normal lung, a lung cancer subject with good prognosis, and a lung cancer subject with poor prognosis are useful as control reagents in the context of the present invention. Furthermore, PKP3 expressing cells may also be prepared by transfecting a suitable host cell with a PKP3 expressing vector. The transformant expressing PKP3 can be used as control reagent. In particular, a transformant showing the same PKP3 expression level as that of a lung cancer sample associated with good prognosis, and a lung cancer sample with poor prognosis are preferable control reagents useful in the comparison step of the present invention. The control instructions (e.g., written, tape, CD-ROM, etc.) for carrying out the assay may also be included in the kit. The assay format of the kit may be a Northern hybridization or a sandwich ELISA, both of which conventional in the art.

For example, a PKP3 detection reagent may be immobilized on a solid matrix, such as a porous strip, to form at least one PKP3 detection site. The measurement or detection region of the porous strip may include a plurality of sites, each containing a nucleic acid. A test strip may also contain sites for negative and/or positive controls. Alternatively, control sites may be located on a strip separate from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of PKP3 present in the sample. The detection sites may be configured in any suitably detectable shape and are typically in the shape of a bar or dot spanning the width of a test strip.

In addition, immunohistochemical analysis is also a well known technique for evaluating the level of a protein in a tissue sample. For example, a PKP3 detection reagent comprising an anti-PKP3 antibody (first antibody) may be labeled with signal generating molecules via direct linkage or an indirect labeling technique. Anti-immunoglobulin antibody recognizing the first antibody can be used as the second antibody for indirect labeling technique of the first antibody. The second antibody may be labeled with suitable signal generating molecule or binding ligand, such as biotin. Any enzymes, chromophore, fluorophore, and luminophore can be used as signal generating molecule for the immunohistochemical analysis. The biotin ligand further may bind avidin-peroxidase.

Although methods and materials similar or equivalent to those described herein can be used in the practice or testing of the present invention, suitable methods and materials are described below. However, the following examples are only intended to illustrate the present invention and to assist one of ordinary skill in making and using the same. Accordingly, the examples are not intended in any way to otherwise limit the scope of the invention.

EXAMPLES

Example 1

Materials and Methods (a) Immunohistochemistry and Tissue Microarray

To investigate the presence of PKP3 protein in clinical samples (normal lung tissues and NSCLCs that had been embedded in paraffin blocks), sections were stained using ENVISION+ Kit/horseradish peroxidase (HRP) (DakoCytomation, Glostrup, Denmark). Briefly, a mouse monoclonal anti-human PKP3 antibody was added after blocking endogenous peroxidase and proteins, and the sections were incubated with HRP-labeled anti-mouse IgG as the secondary antibody. Substrate-chromogen was added and the specimens were counterstained with hematoxylin.

Tumor-tissue microarrays were constructed using the 293 formalin-fixed NSCLCs described previously (Kononen J, et al. (1998) Nat Med 4(7):844-7.; Chin S F, et al. (2003) Mol Pathol 56(5):275-9.; Callagy G, et al. (2003) Diagn Mol Pathol 12(1):27-34.; Sauter G, et al. (2003) Nat Rev Drug Discov 2(12):962-72.). Each area for sampling was selected on the basis of visual alignment with the corresponding HE-stained section on a slide. Three, four, or five tissue cores (diameter 0.6 mm; height 3-4 mm) taken from each donor tumor block were placed into a recipient paraffin block by means of a tissue microarrayer (Beecher Instruments, Sun Prairie, Wis.). A core of normal tissue was punched from each case, and 5-μm sections of the resulting microarray block were used for immunohistochemical analysis.

PKP3 levels were assessed semi-quantitatively according to staining intensity as absent (scored as 0), weak (scored as 1+) or strongly positive (scored as 2+) by three independent investigators without prior knowledge of the clinical follow-up data. Cases were accepted only as strongly positive if reviewers independently defined them as such. Contingency tables were used to analyze the relationship of PKP3 expression to lymph-node metastasis and tumor stage in NSCLC patients; correlation with patient survival was assessed by the Kaplan-Meier method. Statistical differences between the groups were determined with the Log-rank test. Tumor-specific survival data were obtained by reviewing hospital records and/or by communication with attending physicians. A total of 279 patients (155 ADCs, 95 SCCs, 15 LCCs, 10 BACs, and 4 ASCs) were evaluated from the time of surgery to the last known follow-up.

Example 2

Association of High PKP3 Expression with Disease Progression

PKP3 expression was examined in clinical lung cancers using tissue arrays. Positive staining appeared predominantly in the plasma membrane and/or cytoplasm, and weakly (as speckles) in some nuclei in 98% of ADCs (157/160), 97% of SCCs (99/102), 94% of LCCs (16/17), 100% of BACs (10/10), and 100% of ASCs (4/4). All of those tumors were surgically-resectable NSCLCs, and no staining was observed in any of their adjacent normal lung tissues (FIGS. 1A-D). A pattern of PKP3 expression was classified on the tissue array as ranging from absent/weak (scored as 0~1+) to strong (scored as 2+). Strong PKP3 staining was not associated with any of the clinicopathological factors in SCCs. However in ADCs, expression levels of PKP3 were significantly associated with node status (N0 vs N1, N2: $P=0.0017$; chi-square test) and clinical stage (stage I vs II, IIIa: $P=0.009$; chi-square test). The sample sizes of LCCs, BACs, and ASCs were too small to be evaluated further.

Levels of PKP3 expression were investigated to determine is an association with tumor-specific survival time existed. Strong PKP3 staining did not correlate with poor tumor-specific survival among SCC patients ($P=0.66$ by the Log-rank test); however, ADC patients whose tumors over-expressed PKP3 suffered shorter tumor-specific survival as compared to those with absent/weak PKP3 expression ($P=0.009$ by the Log-rank test; FIG. 1E). Using univariate analysis, it was determined that clinical stage ($P=0.0001$; score test), node status ($P<0.0001$; score test), tumor size (T1 vs T2, T3, T4: $P=0.0076$; score test), and high PKP3 expression ($P=0.009$; score test) were important correlative features for poor prognoses of patients with ADC.

Industrial Applicability

The present inventors have shown that plakophilin 3 (PKP3) as utility as a prognostic indicator of lung cancers and the present invention accordingly provides the method of assessing or determining a non-small cell lung cancer (NSCLC) prognosis. Thus, the present invention will enable clinicians to choose, in advance, the most appropriate treatment for each individual NSCLC patient, even without the information of conventional clinical staging of the disease and using only routine procedures for tissue-sampling. All patents, patent applications, and publications cited herein are incorporated by reference herein in their entirety.

While the invention has been described in detail and with reference to specific embodiments thereof, it will be apparent to one skilled in the art that various changes and modifications can be made therein without departing from the spirit and scope of the invention.

The invention claimed is:

1. A method of assessing a lung adenocarcinoma prognosis, wherein the method comprises the steps of:
   a. detecting a PKP3 expression level in lung adenocarcinoma cells surgically collected from a subject diagnosed with lung adenocarcinoma,
   b. comparing the expression level of PKP3 detected in step (a) with a control level of PKP3 expression associated with positive prognosis, and
   c. determining a poor prognosis after surgery when the PKP3 expression level detected is elevated as compared to the level associated with positive prognosis.

2. The method of claim 1, wherein the PKP3 in the lung adenocarcinoma cells is detected by:
   a. contacting the lung adenocarcinoma cells with an antibody recognizing the PKP3 protein; and
   b. detecting the antibody bound to the lung adenocarcinoma cells.

* * * * *

UNITED STATES PATENT AND TRADEMARK OFFICE
CERTIFICATE OF CORRECTION

| | | |
|---|---|---|
| PATENT NO. | : 8,034,578 B2 | Page 1 of 1 |
| APPLICATION NO. | : 11/577485 | |
| DATED | : October 11, 2011 | |
| INVENTOR(S) | : Yusuke Nakamura et al. | |

It is certified that error appears in the above-identified patent and that said Letters Patent is hereby corrected as shown below:

Please correct the following Claim, as indicated below:

In Claim 1, column 15, section (b), please delete "control".

Signed and Sealed this
Tenth Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,034,578 B2 | Page 1 of 1 |
| APPLICATION NO. | : 11/577485 | |
| DATED | : October 11, 2011 | |
| INVENTOR(S) | : Yusuke Nakamura et al. | |

It is certified that error appears in the above-identified patent and that said Letters Patent is hereby corrected as shown below:

Please correct the following Claim, as indicated below:

Column 15, line 21 (Claim 1, line 7) please delete "control".

This certificate supersedes the Certificate of Correction issued January 10, 2012.

Signed and Sealed this
Fourteenth Day of February, 2012

David J. Kappos
*Director of the United States Patent and Trademark Office*